United States Patent [19]

Haber et al.

[11] Patent Number: 5,246,670
[45] Date of Patent: Sep. 21, 1993

[54] PHARMACEUTICAL MIXING CONTAINER WITH BUOYANT MIXING ELEMENT

[75] Inventors: Terry M. Haber, Lake Forest; Clark B. Foster, Laguna Niguel; William H. Smedley, Lake Elsinore, all of Calif.

[73] Assignee: Habley Medical Technology Corporation, Laguna Hills, Calif.

[21] Appl. No.: 949,651

[22] Filed: Sep. 23, 1992

[51] Int. Cl.[5] .................. B01L 3/00; B65D 25/08; A61M 5/00

[52] U.S. Cl. ............................ 422/102; 206/220; 366/130; 422/99; 422/100; 604/187; 604/218; 604/232; 604/403; 604/416

[58] Field of Search .............. 206/220; 222/394; 366/129, 130; 422/99, 100, 102, 104; 604/82, 187, 218, 232, 403, 416

[56] References Cited

U.S. PATENT DOCUMENTS

| | | | |
|---|---|---|---|
| 2,229,739 | 1/1941 | Harrington | 604/403 |
| 2,487,236 | 11/1949 | Greenberg | 206/220 |
| 2,720,880 | 10/1955 | Whitaker et al. | 604/232 |
| 2,870,766 | 1/1959 | Dann et al. | 604/232 X |
| 3,295,525 | 1/1967 | Evers et al. | 604/232 X |
| 3,756,390 | 9/1973 | Abbey et al. | 604/416 X |
| 3,796,303 | 3/1974 | Allet-Coche | 604/416 X |
| 3,826,261 | 7/1974 | Killinger | 604/416 |
| 3,888,113 | 6/1975 | Miranda | 422/102 X |
| 4,182,447 | 1/1980 | Kay | 206/220 |
| 4,256,461 | 3/1981 | Wallace et al. | 422/99 X |
| 4,289,648 | 9/1981 | Hoskins et al. | 604/416 X |
| 4,381,779 | 5/1983 | Marguiles | 604/232 X |
| 4,473,530 | 9/1984 | Villa-Real | 422/104 X |
| 4,723,945 | 2/1988 | Theiling | 604/232 |
| 4,850,966 | 7/1989 | Grau et al. | |

Primary Examiner—James C. Housel
Assistant Examiner—Milton I. Cano
Attorney, Agent, or Firm—Townsend and Townsend Khourie and Crew

[57] ABSTRACT

A pharmaceutical mixing container for storing a liquid having at least two factions which tend to separate during storage. A housing has an inner volume and is closed at one end by a septum arrangement and at another end by a slidable sealing member. A buoyant member is located within the housing and floats within the liquid faction of the pharmaceutical contained within the housing. By manually translating and rotating the housing, the buoyant member is forcibly moved along the liquid surface causing gentle turbulent waves which provide thorough admixing for the pharmaceutical constituents without causing mechanical damage to delicate constituents, such as crystalline factions found in NPH type insulin.

10 Claims, 2 Drawing Sheets

PHARMACEUTICAL MIXING CONTAINER WITH BUOYANT MIXING ELEMENT

BACKGROUND OF THE INVENTION

This invention relates to containers for liquids having a miscible component. More particularly, this invention relates to mixing containers for storing a liquid pharmaceutical.

Containers are known for storing a pharmaceutical having a liquid component and a second component miscible with a liquid component. A typical container of this type is filled with the pharmaceutical and stored for later use. Some pharmaceuticals separate into their individual components when left in storage. For example, liquid NPH insulin has a crystalline faction which must be in solution in order to be effectively administered. During storage in a container, such crystals precipitate out of the liquid solution and must be thoroughly mixed with the liquid faction just prior to administration. Admixture of the crystalline faction and the liquid faction has been achieved in the past in a number of different ways. One such technique is to provide a mixing element which is freely moveable within the container, in a similar manner to the mixing ball found in ordinary aerosol spray cans. This solution has been found to be less than desirable, since the crystalline faction is composed of delicate crystals which should not be mechanically damaged or ruptured during the mixing process. The use of a freely moveable mixing element within the container, however, has been found to damage and rupture the crystals, which severely impairs the effectiveness of the pharmaceutical. Efforts in the past to provide a pharmaceutical mixing container with a freely moveable mixing element devoid of the above disadvantage have not been successful to date.

SUMMARY OF THE INVENTION

The invention comprises a pharmaceutical mixing container with a freely moveable element contained therein which is capable of providing gentle mixing action to thoroughly admix separated components in a pharmaceutical without mechanically damaging those components.

A pharmaceutical mixing container for storing a liquid having at least two miscible components includes a housing having a first end, a second end and a wall structure defining an inner volume, the housing preferably having cylindrical geometry. A closure member providing a fluid seal is arranged at the first end of the housing, the closure member preferably including a septum and a retaining band for securing the septum to the first end of the housing. A sealing member is positioned at least partially within the housing, preferably adjacent the second end, and provides a second fluid seal for containing the liquid within the housing. A buoyant member having a specific gravity less than that of the liquid to be contained is located within the inner volume of the housing, the buoyant member preferably comprising a hollow sphere fabricated from glass, ceramic, inert plastic such as polypropylene, polyethylene or the like.

In use, the liquid is stored within the container and is admixed prior to administration by imparting motion to the housing, typically by manual translation and rotation of the housing. During such motion, the buoyant member is maneuvered within the inner volume and motion of the buoyant member generates turbulent wake currents within the liquid. Since the mass of the buoyant member is relatively small, mechanical damage to the constituents being admixed is minimized or eliminated.

The liquid may be hydraulically withdrawn from the inner volume of the housing by penetrating the septum with a needle cannula of a syringe and subsequently operating the syringe. The liquid may also be expelled from the inner volume of the housing by penetrating the septum with a double-ended needle and forcibly ejecting the liquid using a drive stem coupled to the sealing member and translating the sealing member with the drive stem in the direction of the first end.

While the invention may be employed with a wide variety of miscible pharmaceutical components, it is ideally suited for use with any pharmaceutical having a liquid faction and a crystalline faction requiring admixture prior to use. In particular, the gentle mixing afforded by the buoyant member is sufficient to thoroughly admix the constituents without damaging the crystal structure.

For a fuller understanding of the nature and advantages of the invention, reference should be had to the ensuing detailed description taken in conjunction with the accompanying drawings.

DESCRIPTION OF THE PREFERRED EMBODIMENTS

Figure 1:
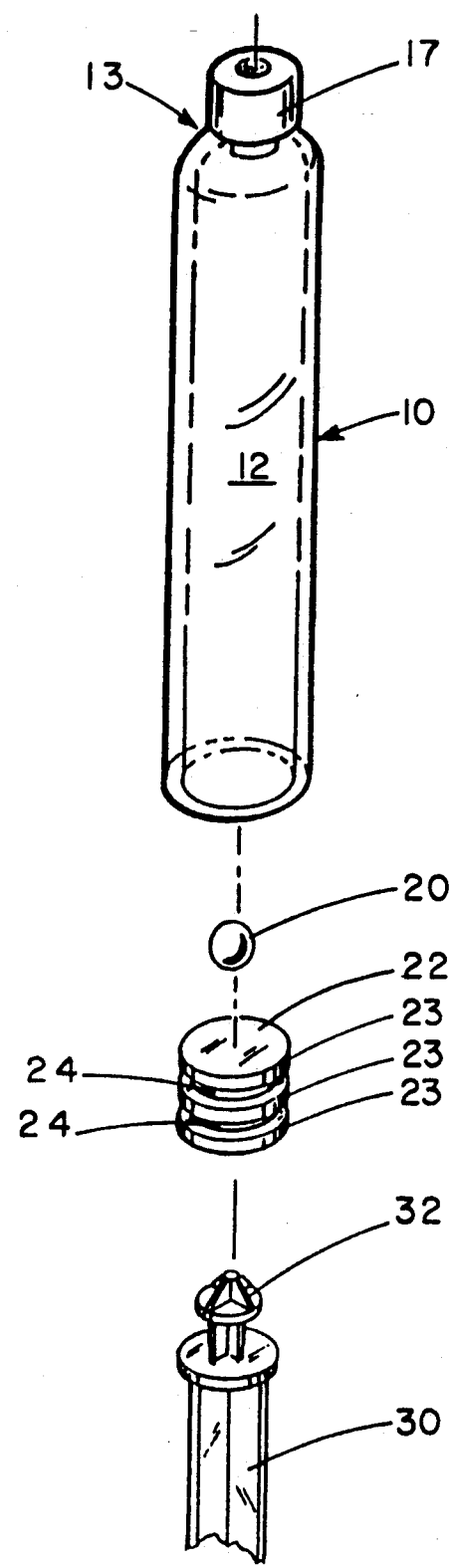
FIG. 1 is an exploded perspective view showing the preferred embodiment of the invention.
Figure 2:
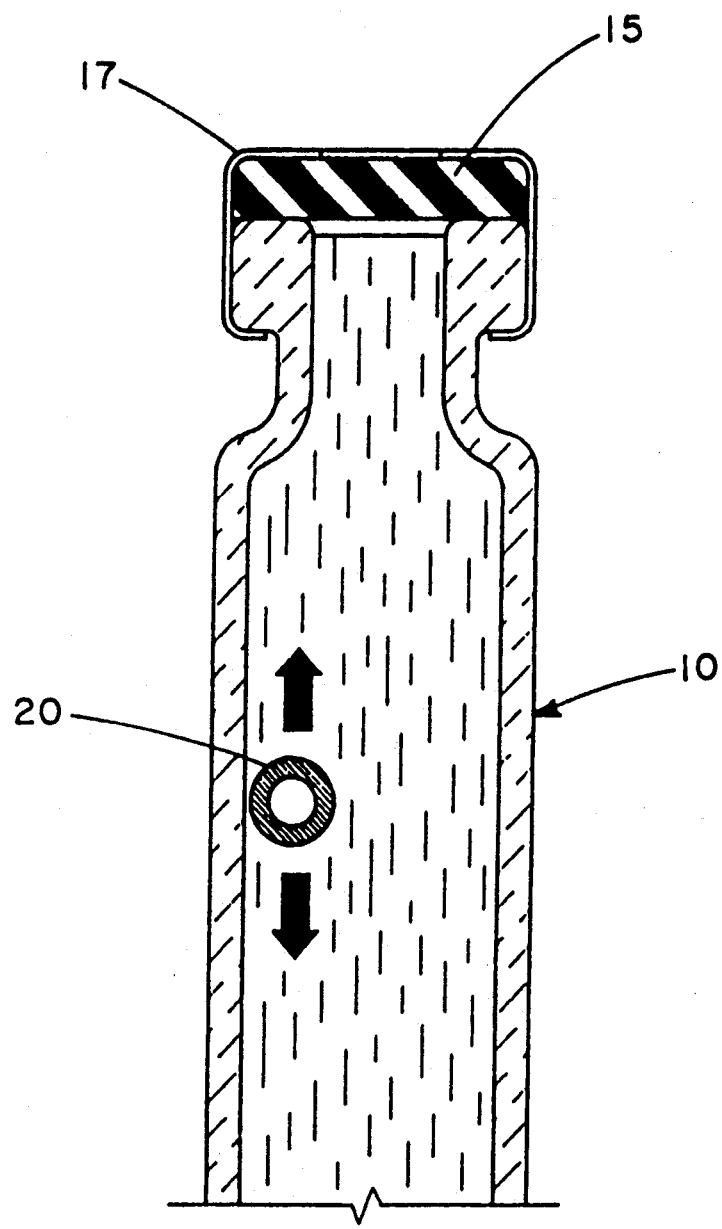
FIG. 2 is a sectional view of the assembled device showing the upper portion of the housing.

Turning now to the drawings, FIG. 1 illustrates a preferred embodiment of the invention. As seen in this Fig., a housing generally designated with reference numeral 10 has a generally cylindrical geometrical configuration defining an inner volume 12, a distal end 13 and a proximal end 14. Housing 10 may be fabricated from glass or any suitable plastic material which is compatible with the pharmaceutical to be contained therewithin. Secured to distal end 13 is a closure member comprising an elastomeric septum 15 which is retained to first end 13 by means of a metal band 17. Septum 15 and band 17 are fabricated and arranged in such a manner that access to the inner volume 12 may be gained by penetrating the band 17 and septum 15 with a needle-like probe, such as a needle cannula of a syringe or a double ended syringe needle.

A buoyant member 20, shown as a hollow sphere, is contained within inner volume 12. Buoyant member 20 may be fabricated from a wide variety of materials, such as glass, ceramic, inert plastic such as polypropylene, polyethylene or the like. The structure and size of buoyant member 20 are selected in such a manner that the specific gravity of member 20 is less than that of the liquid to be contained within volume 12.

A sealing member 22 having an outer diameter providing a sealing engagement with the inner walls of housing 10 is installed adjacent the proximal end 14 of housing 10. Sealing member 22 may be fabricated from a wide variety of suitable materials, such as butyl rubber, silicone rubber or the equivalent. Sealing member 22 functions to provide a fluid seal for the lower end of inner volume 12. To this end, sealing member 22 is provided with a plurality of lands 23 and grooves 24 along the outer surface thereof.

Attached to sealing member 22 is a drive stem 30 for enabling manual expulsion of the liquid within inner volume 12 when the liquid has been admixed and is ready to be dispensed. Drive stem 30 is provided with mechanical coupling element 32, which provides a press fit within a corresponding recess (not shown) within the hollowed-out interior of sealing member 22. Other mechanical arrangements for coupling drive stem 30 to sealing member 22 will occur to those skilled in the art.

In use, the buoyant member 20 is placed within inner volume 12 and sealing member 22 is installed from the proximal end 14 of housing 10. The inner volume 12 is then filled with the pharmaceutical liquid, and septum 15 and closure band 17 are installed to seal volume 12.

When the pharmaceutical is to be administered, the housing 10 is manipulated by the user in such a manner that the buoyant member 20 is translated about the inner volume 12 of housing 10. This motion provides turbulent wake currents within the liquid so that the constituent ingredients are admixed without mechanically damaging any delicate constituents, such as the crystalline faction found in NPH type insulin. After thorough admixture, the septum 15 is penetrated by means of a needle cannula of a syringe or a double-ended needle and the liquid is withdrawn from inner volume 12.

As will now be apparent, the buoyant member is capable of providing thorough admixture of the pharmaceutical constituent ingredients in a relatively simple and expedient fashion. In addition, the container fabricated according to the invention is relatively simple and inexpensive to manufacture, can be readily filled with the appropriate liquid pharmaceutical, and can easily be employed for administering the pharmaceutical to a patient.

While the above provides a full and complete disclosure of the preferred embodiments of the invention, various modifications, alternate constructions and equivalents may occur to those skilled in the art. For example, while buoyant member 20 has been illustrated as a sphere, other geometries may be employed, as desired. In addition, other mechanical arrangements may be used to provide the translatory motion for sealing member 22 when it is desired to expel the liquid from inner volume 12. Further, the slidable sealing member 22 may be omitted in some applications and the inner volume 12 may be sealed by a solid housing bottom wall or a wall formed internally of the housing walls. Therefore, the above descriptions should not be construed as limiting the scope of the invention, which is defined by the appended claims.

What is claimed is:

1. A pharmaceutical mixing container for storing a liquid with a miscible component, said container comprising:
   a housing having a first end, a second end and a wall structure defining an inner volume;
   a closure member at said first end providing a first fluid seal;
   means for providing a second fluid seal so that said inner volume is closed; and
   a buoyant hollow member located within said inner volume, said buoyant member having a specific gravity less than that of the liquid to be contained so that the liquid can be gently mixed by imparting motion to said housing.

2. The container of claim 1 wherein said buoyant hollow member comprises a sphere.

3. The container of claim 2 wherein said sphere is fabricated from a material selected from the group consisting of glass, ceramic and an inert plastic.

4. The container of claim 1 wherein said closure member comprises a septum.

5. The container of claim 4 wherein said closure member further includes a retaining band.

6. The container of claim 1 wherein said housing has cylindrical geometry.

7. The container of claim 1 wherein said means for providing a second fluid seal is located adjacent said second end.

8. The container of claim 1 wherein said second fluid seal providing means comprises a sealing member having a portion positioned within said housing.

9. The container of claim 8 further including means for enabling the liquid within the container to be ejected from said first end when said closure member is opened.

10. The container of claim 9 wherein said sealing member is slidably received by said housing; and wherein said enabling means comprises a drive stem coupled to said sealing member.

* * * * *